United States Patent [19]
Engstrom et al.

[11] Patent Number: 5,753,259
[45] Date of Patent: *May 19, 1998

[54] METHOD OF PREPARING CONTROLLED-RELEASE PREPARATIONS FOR BIOLOGICALLY ACTIVE MATERIALS AND RESULTING COMPOSITIONS

[75] Inventors: Sven Engstrom, Lund; Kare Larsson, Bjarred; Bjorn Lindman, Lund, all of Sweden

[73] Assignee: GS Development AB

[*] Notice: The term of this patent shall not extend beyond the expiration date of Pat. No. 5,151,272.

[21] Appl. No.: 313,543

[22] Filed: Sep. 27, 1994

Related U.S. Application Data

[63] Continuation of Ser. No. 910,616, Jul. 8, 1992, abandoned, which is a continuation of Ser. No. 540,441, Jun. 18, 1990, Pat. No. 5,151,272, which is a continuation of Ser. No. 166,759, Mar. 3, 1988, abandoned, which is a continuation of Ser. No. 638,221, filed as PCT/SE83/00411 Nov. 25, 1983, abandoned.

[30] Foreign Application Priority Data

Nov. 26, 1982 [SE] Sweden ................... 8206744

[51] Int. Cl.$^6$ ........................ A61K 9/127
[52] U.S. Cl. ............ 424/450; 264/4.1; 264/4.3; 264/4.6
[58] Field of Search ............ 264/4.1, 4.3, 4.6; 428/402.2; 424/84, 450, 498, 502; 436/829; 514/963, 965

[56] References Cited

U.S. PATENT DOCUMENTS

| | | | |
|---|---|---|---|
| 4,073,943 | 2/1978 | Wretlind et al. | 514/938 X |
| 4,115,313 | 9/1978 | Lyon et al. | 252/312 X |
| 4,145,410 | 3/1979 | Sears | 424/450 |
| 4,156,719 | 5/1979 | Sezaki | 424/118 |
| 4,217,344 | 8/1980 | Vanlerberghe et al. | 264/4.1 X |
| 4,235,871 | 11/1980 | Papahadjopoulos et al. | 424/450 |
| 4,241,046 | 12/1980 | Papahadjopoulos et al. | 424/450 |
| 4,323,556 | 4/1982 | DalMoro et al. | 424/84 |
| 4,331,654 | 5/1982 | Morris | 424/450 |
| 4,377,567 | 3/1983 | Geho | 514/4 X |
| 4,789,633 | 12/1988 | Huang | 435/240.2 |
| 5,143,934 | 9/1992 | Lading | 514/396 |
| 5,151,272 | 9/1992 | Engstrom | 424/450 |
| 5,262,164 | 11/1993 | Damani | 424/422 |

FOREIGN PATENT DOCUMENTS

| | | |
|---|---|---|
| 0041772 | 1/1981 | European Pat. Off. . |
| 65/26837 | 11/1965 | Japan . |
| 2069133 | 8/1981 | United Kingdom ........... 436/829 |

OTHER PUBLICATIONS

Gregoriadis: "The Carrier Potential of Liposomes in Biology and Medicine", The New England Journal of Medicine, vol. 295, No. 13, pp. 704–710, Sep. 23, 1976.

First page from The Journal of Physical Chemistry, 1988 92, 2261.

F. Gstirner, Grundstoffe and Verfahren der Arzneibereitung, Ferdinand Enke Verlag, Stuttgart, 1960, pp. 454–455.

S.G. Frank, Acta Pharm. Suec. 13, 41–42 (1976).

Linstrom et al "Aqueous Lipid Phases of Relevance to Intestinal Fat Digestion and Absorption", Lipids, vol. 16, No. 10, Oct. 1981, pp. 749–754.

Svard et al "Micelles, Vesicles and Liquid Crystals in the Monoolein—Sodium Taurocholate—Water System".

Ulmius et al "Molecular Organization in the Liquid–Crystalline Phases of Lecithin–Sodium Cholate–Water Systems . . ." Biochemistry 1982, 1553–1560, Surfactants in Solution, vol. 1.

Edited by K.L. Mittal et al, Plenum Publ. Corp. (1984) pp. 143–152. Gutman et al "31$_p$ and 2$_H$ NMR Studies . . . ".

Primary Examiner—Gollamudi S. Kishore
Attorney, Agent, or Firm—Kirkland & Ellis

[57] ABSTRACT

A method and product for preparing a controlled-release composition are provided. The method comprises formation of a mixture containing at least one amphiphilic substance capable of forming a liquid crystalline phase, in contact with a liquid selected from the group consisting of water, glycerol, ethylene glycol, propylene glycol and mixtures thereof. The method includes a step of providing in such mixture a bioactive material.

19 Claims, 4 Drawing Sheets

METHOD OF PREPARING CONTROLLED-RELEASE PREPARATIONS FOR BIOLOGICALLY ACTIVE MATERIALS AND RESULTING COMPOSITIONS

BACKGROUND OF THE INVENTION

The present application is a Continuation of application Ser. No. 07/910,616, filed Jul. 8, 1992 and with the present application at the time of filing, but now abandoned. Application Ser. No. 07/910,616 is a Continuation of Ser. No. 07/540,441, filed on Jun. 18, 1990 (now U.S. Pat. No. 5,151,272), which is a Continuation of Ser. No. 07/166,759, filed Mar. 3, 1988 (now abandoned), which is a Continuation of Serial No. 06/638,221, filed Jul. 26, 1984 (now abandoned). The parent to the present application was a national stage application corresponding to PCT Application No. SE83/00411, filed Nov. 25, 1983, which is turn claims priority form Swedish application 8206744-8, filed Nov. 26, 1982.

Amphiphilic substances, i.e. substances with both hydrophilic and hydrophobic (lipophilic) groups, spontaneously tend to self-associate in aqueous systems forming various types of aggregates. A typical example is shown in FIG. 1 in "Cubic Mesomorphic Phases" (R. R. Balmbra, J. S. Clunie and J. F. Goodman, Nature, 222, 1159 (1969)), in which an increasing amount of amphiphile in water gives rise to micellar, cubic, hexagonal and lamellar phases. The structures of these phases are well-known, except for the cubic phases, since there are a number of cubic phases, some of which remain to be determined in detail.

Several important features of the above mentioned phases are listed below:

a) All phases are thermodynamically stable and have therefore no tendency to phase separate with time (unless chemical decomposition occurs), and they will also form spontaneously.

b) All phases are characterized by having distinct hydrophilic and hydrophobic domains, which give them the possibility to dissolve (solubilize) or disperse both water-soluble and water-insoluble compounds.

c) In general the rheology of the phases varies from low viscous Newtonian (dilute or moderately concentrated micellar phases) over viscous liquids to visco-elastic rigid systems (cubic phases.

d) The long-range order in the hexagonal, lamellar and cubic phases, as seen inter alia in X-ray low angle diffraction, in combination with liquid-like properties on a molecular level, have given rise to the notation "liquid crystalline phases". The anisotropic phases, i.e. mainly the hexagonal and the lamellar phases, are birefringent and are therefore easily identified in the polarizing microscope.

e) If oil, in a broad sense, is added to an amphiphile-water system, and the oil/water ratio is high (>>1), then aggregates of the reversed type may form, i.e. reversed micellar and reversed hexagonal, or alternatively, cubic structures can be obtained. These structures will also give rise to thermodynamically stable phases.

f) The occurrence of the above described phases is not restricted to specific amphiphiles, but they are encountered in almost every amphiphile-oil-water system. One or two phases may be absent, and the location of the phases vary in the phase diagram, but it is not unjustified to state that the similarities are more pronounced than the differences.

Several of the characteristics listed above make some of the phases formed in systems with amphiphilic substances interesting candidates for being used as matrices or barriers in controlled-release preparations. Perhaps the most important feature is the possibility to dissolve both water-soluble and water-insoluble compounds in the phases due to their amphiphilic character. Moreover, the highly ordered structures with distinct hydrophilic and hydrophobic domains put restrictions on the diffusion of added compounds, a fact which may be advantageously used for controlled-release purposes. Especially the cubic liquid crystalline phases offer many possibilities in this context due to their rheological properties, which make them useful both as tablets and pastes.

The cubic liquid crystalline phase may crudely be characterized as being either of the water-discontinuous or oil-discontinuous droplet type, or of the bi-continuous type. The droplet structures may thus be either of a "water-soluble" or of a "water-insoluble" type. Bi-continuous structures of cubic phase have been determined by V. Luzatti et al. (Nature, 215, 701 (1967)) and K. Larsson et al. (Chem. Phys. Lipids, 27, 321 (1980)). All the different forms of cubic phases can be used in controlled-release preparations which the following discussion will explain.

The cubic liquid crystalline phase can also be described as erodible or non-erodible depending on its behaviour in excess water. Furthermore, the rate of erosion depends on, besides temperature and agitation, the appearance of the phase diagram for the actual amphiphile. This dependence is extremely strong and the rate of erosion may vary by several orders of magnitude. The following three examples will illustrate the erodible and non-erodible types of cubic phases at a temperature of 37° C.

In FIG. 11 in "Phase Behaviour of Polyoxyethylene Surfactants with Water" m (D. J. Mitchell, G. J. T. Tiddy, L. Waring, T. Bostock and M. P. McDonald, J. Chem. Soc. Faraday Trans. 1, 79, 975 (1983)) two cubic phases are found, one at low and the other at high amphiphile concentration. The cubic phase at low concentration is built up by closed-packed micelles and this phase will erode fast in water giving a micellar solution. For the cubic phase at high concentration of amphiphile, however, the rate of erosion is much slower since it, in excess water, first is converted to a hexagonal phase, then to the other type of cubic phase which finally forms a micellar phase.

For the second case, FIG. 2 in "Optically Positive, Isotropic and Negative Lamellar Liquid Crystalline Solutions", (J. Rogers and P. A. Winsor, Nature, 216, 477 (1967)), the situation is in part similar to the cubic phase at high amphiphile concentration in the first example, except that now the cubic phase is converted to a lamellar phase, which then turns into a micellar solution. In this system the micelles are the thermodynamically rather unstable as demonstrated by a low solubility of surfactant in aqueous solution. This will have the effect of decreasing the rate of erosion.

The third example, FIG. 7 (monoolein-water) in "Food Emulsifiers and Their Associations with Water" (N. Krog and J. B. Lauridsen, in "Food Emulsions" (ed. S. Friberg), Marcel Dekker Inc. (1976)), shows a cubic phase which will, when in water, be in equilibrium with a monomer solution of amphiphile in water ($10^{-6}$M). This cubic phase will stay unchanged in excess water (at least for extremely long times).

The choice of an erodible or a non-erodible cubic phase in a controlled-release preparation depends on the required rate profile, the solubility of the compound, which rate one wants to control etc. For example, if the active substance is an almost water-insoluble drug, an eroding cubic phase may act as a source for molecularly dissolved drug. Of course, the use of erodible cubic phases is not limited to water-insoluble compounds, but may also be used if a relatively fast release profile is desired, or if an initial protection of a pharmaceutical compound (which may be subject to chemical degradation in contact with the high acidity of the gastric juice) is required.

Non-eroding cubic phases, stable in water, may be used for applications where longer release times are desirable. Both water-soluble and water-insoluble compounds can be used in this kind of cubic phase. The release rate of a bioactive substance from a non-erodible cubic phase may either be determined by the outer surface of the cubic phase towards the surrounding aqueous medium or the interfaces between hydrophilic and hydrophobic domain within the cubic phase, depending on whether the cubic phase is mono- or bi-continuous and the nature (hydrophilic, hydrophobic or amphiphilic) of the bioactive compound.

Fine adjustments of the release rate in any kind of cubic phase can be made by the addition of salt, glycerol, ethylene glycol, propylene glycol or any similar amphiphile of low molecular weight.

Other techniques of employing amphiphilic molecules to encapsulate biologically active materials for controlled-release purposes are described in U.S. Pat. Nos. 4,016,100; 4,145,410; 4,235,871 and 4,241,046. In these applications aggregates of other structures are involved and, furthermore, they have all in common that the amphiphile-water preparations of these methods are thermodynamically unstable (dispersions, emulsions and vesicles) and consist of at least two phases. The present invention is therefore fundamentally different from these, since the controlled-release matrices or barriers prepared by our technique will be thermodynamically stable one phase compositions. Because of the regular structure, with exact crystallographic lattices, the present invention provides a highly reproducible controlled-release system contrary to solutions involving polymers.

SUMMARY OF THE INVENTION

Our invention relates to a method for preparing a controlled-release composition for biologically active materials, the composition consisting of chemical substances capable of forming a cubic liquid crystalline phase, or any other type of liquid crystalline phase, and the bioactive material, the method which comprises:

forming a mixture of one or more amphiphilic substances in amounts necessary to form a cubic liquid crystalline phase when placed in contact with at least one liquid selected from the group including water, glycerol, ethylene glycol and propylene glycol, adding the biologically active material to said mixture.

The invention also comprises the intermediate phases formed, the product cubic phases, their use and carrier compositions including the cubic phases as the active ingredient thereof.

The terms "biologically active material" and "bioactive material" as used throughout the specification and claims mean a compound or composition which, when present in an effective amount, reacts with and/or affects living cells and organisms.

The term "liquid crystalline phase" as used herein denotes an intermediate state between solid crystals and isotropic liquids, characterized by long-range order and short-range properties close to those of a simple liquid or solution (H. Keller and R. Hatz, in "Handbook of Liquid Crystals", Verlag Chemie, Weinheim(1980)).

The terms "cubic liquid crystalline phase" and "cubic phase" as used herein mean a thermodynamically stable, viscous and optically isotropic phase made of at least amphiphilic substance(s) and water. The cubic phase can be unambiguously identified from the X-ray diffraction pattern.

The term "any other liquid crystalline phase" as used in the claims mean thermodynamically stable optically anisotropic phases like lamellar, hexagonal and reversed hexagonal liquid crystalline phases made of at least amphiphilic substance(s) and water.

The method of the invention is useful to make liquid crystalline phases, especially cubic phases, which in turn are usefully employed in a rich variety of processes. For example, the liquid crystalline phases, may be used to enhance the bioavailability of medications, oral drug delivery, rectal drug delivery, transdermal drug delivery and drug delivery through inhalation. The cubic liquid crystalline phases produced by the method of the invention may also be employed to encapsulate pesticides, feromones, compounds for sustained slow-release to effect the growth of plants and the like.

The precursor of the cubic phase, in the form of a liquid or a solid, as described in claim 1 may also be utilized. When used in the liquid precursor form, a dispersion of the phase can be prepared, which can be utilized as a spray suitable for inhalation.

DESCRIPTION OF THE EMBODIMENTS

The determination of cubic phases

The present invention involves the dissolution or dispersion of a bioactive material in a cubic liquid crystal composed of water and amphiphilic compound(s) or the preparation of a cubic phase in which the bioactive material occurs as an integral part. In the latter case, the cubic phase may form only in the presence of the bioactive active material. When the bioactive material is to be-used only in small amounts, its dissolution in a known cubic phase is a more typical procedure. In many cases, one can in the preparation of controlled-release compositions according to the present invention make use of existing knowledge on phase behaviour of amphiphilic systems. To have a basis for several applications we have studied in some detail samples composed of monoolein, egg yolk lecithin, water and glycerol. By choosing a suitable composition in this system, it has been found feasible to include in the cubic phase appropriate amounts of a large number of bioactive materials and also to control the release rate.

However, it is also useful in a number of contexts to apply cubic phases in other systems. If, in such a case, the phase diagram is not available or, in the case mentioned above, where the existence of a cubic phase may be dependent on the bioactive material used, then some phase studies are a prerequisite to the application of the invention. In particular, the approximate region of existence of the cubic phase (concentrations and temperature) and the phases existing at higher (and depending on mode of employment occasionally also lower) water contents must be determined. Such studies involve visual observations but in particular observations in a polarizing microscope and other techniques. Low angle X-ray diffraction work is needed for the differentiation between different types of cubic phases. During the work on this invention it was found particularly useful to apply nuclear magnetic resonance (NMR) spectroscopy to rapidly scan the phase behaviour of a novel system. Especially $^2$H NMR, working with detracted water, could very effectively distinguish between single- and different multiphase regions and also characterize the degree of anisotropy of a liquid crystalline phase and thus give structural information.

Diffusion rates

The rates of release of bioactive materials according to the present invention can as described above be determined either by an erosion process or a molecular diffusion process or a combination of both. In the case a molecular diffusion process is rate-limiting, useful information on the factors determining the release rate can be obtained in self-diffusion studies. Such self-diffusion measurements are very useful in predicting how and which factors should be modified to obtain a required release rate. Self-diffusion studies in connection with the present invention have been made both using the classical pulsed field-gradient nuclear magnetic resonance spinecho method (E. O. Stejskal and J. E. Tanner, J. Chem. Phys., 42, 288 (1965)) and the novel Fourier transform pulsed-gradient spin-echo technique (P. Stilbs, J. Colloid Interface Sci., 87, 385 (1982)). To illustrate the types of effects encountered some of these results may be mentioned. For a cubic phase of the oil-in-water droplet type in a cationic surfactant-water system consisting of ca. 50% cationic surfactant and ca. 50% water, the self-diffusion of hydrophilic component is ca. 70 times more rapid than the self-diffusion of hydrophobic component. For another cubic phase, of the network bi-continuous type, in the same system and consisting of ca. 80% cationic surfactant and ca. 20% water, the self-diffusion of hydrophilic component is ca. eight times as fast as that of hydrophobic component. For a number of cubic phases built up of anionic surfactant, different hydrocarbons or derivatives thereof and water, self-diffusion coefficients of the order of $10^{-12}$ $m^2s^{-1}$ can be achieved and controlled.

BRIEF DESCRIPTION OF THE DRAWINGS

The monoolein-egg yolk lecithin-water system

The examples below describe the controlled-release properties of the system monoolein-egg yolk lecithin-water using a water-soluble dye (methylene blue) as a model for the bioactive material, reference being made to the accompanying drawings, in which.

Figure 1:
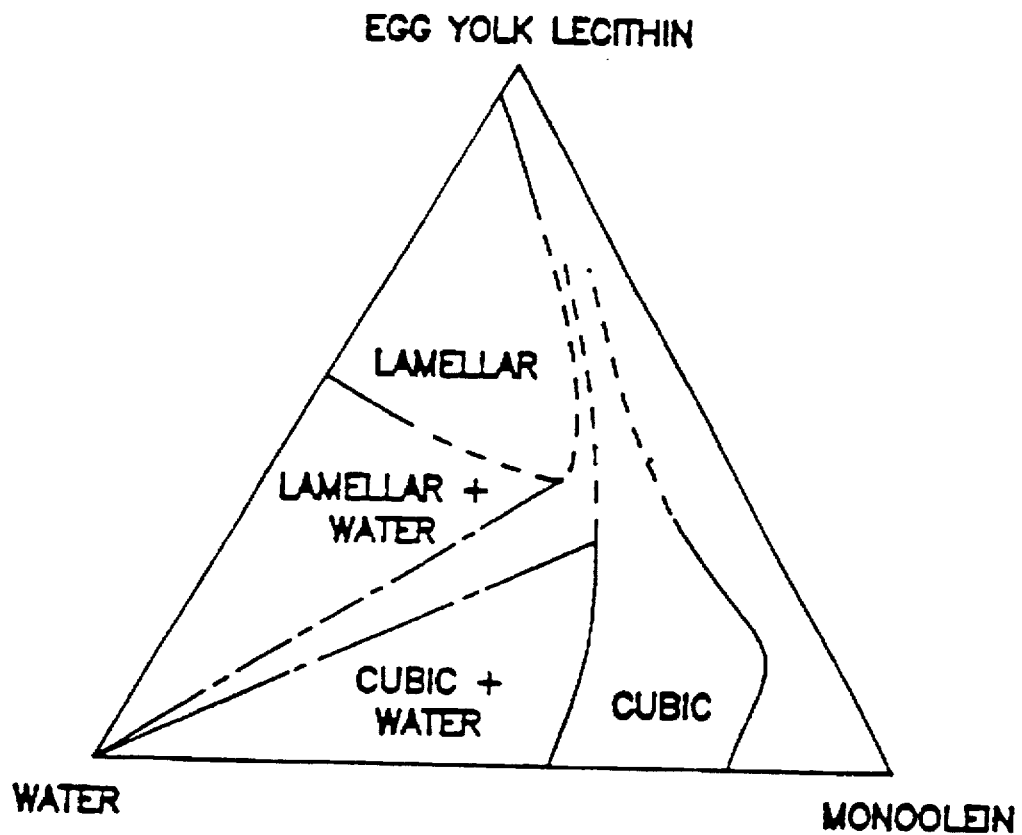
FIG. 1 shows the phase diagram of the ternary system monooleinegg yolk lecithin-water at about 40° C.

An, in many respects, excellent example of an amiphiphilic system which shows the advantages of the present invention is the three-component system monoolein-egg yolk lecithin-water. Its phase diagram is not completely known, but the cubic phase is well established, as seen in FIG. 1. One advantage with this system is the fact that all components occur as natural parts in both animals and plants, which among other things make them attractive for pharmaceutical use. Furthermore, the system offers many possibilities for controlled-release preparations with various properties. For example, by varying the relative amounts of monoolein and egg yolk lecithin, cubic phases of the nonerodible (low lecithin content) or erodible (high lecithin content) type may be formed. The system also allows glycerol, ethylene glycol or propylene glycol to be incorporated to appreciable amounts without destroying the cubic structure. Glycerol is preferred for toxicological reasons and it acts as a highly effective release rate modulator. When water is replaced by glycerol the cubic phase is still formed, with only a minor increase in swelling.

EXAMPLE 1

Figure 2:
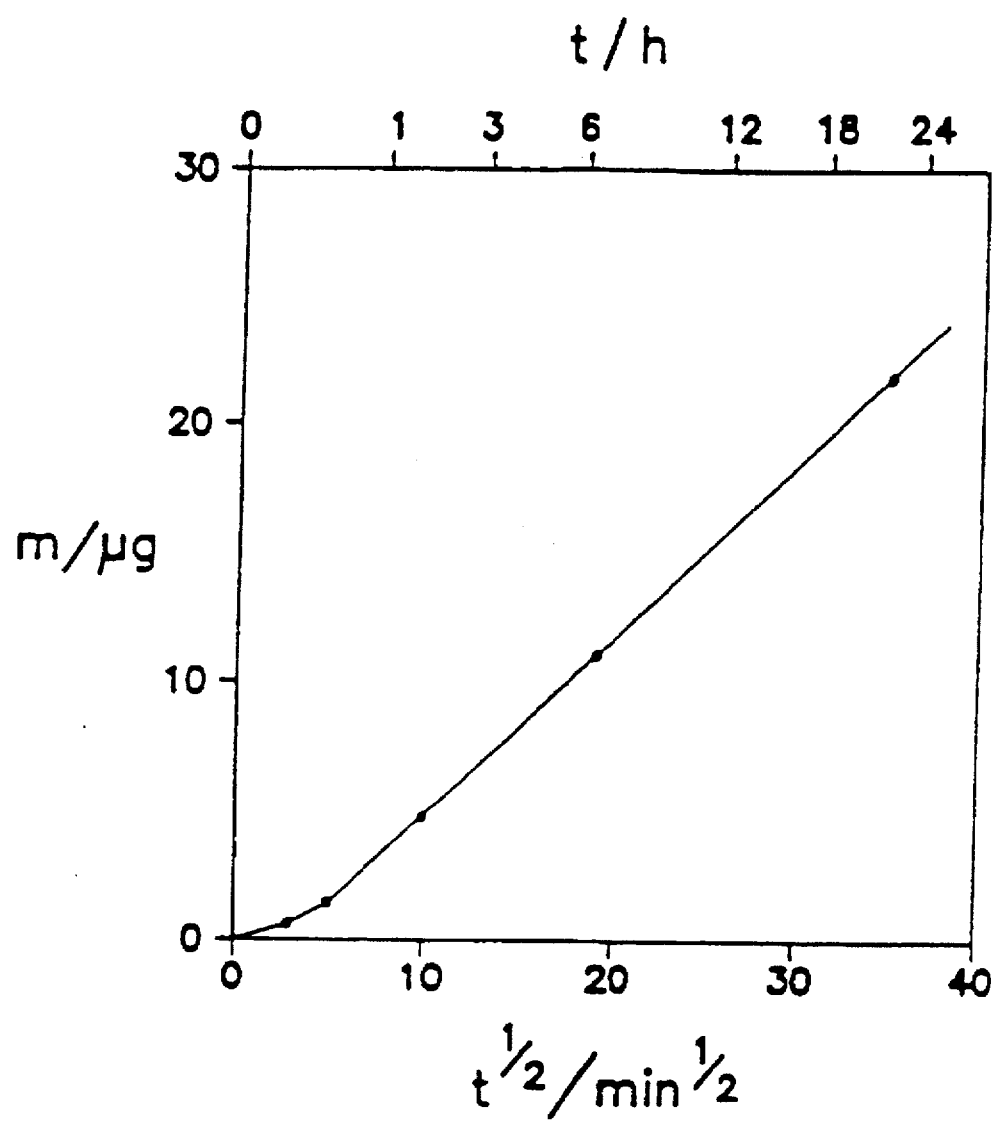
FIG. 2 shows the amount of dye released versus square root of time for the system monoolein-water (including dye) at 37° C.

A cubic liquid crystalline phase is formed by mixing 0.6 g of monoolein (Nu-chek-prep Inc., U.S.A.) and 0.4 g of a 2.8 mM aqueous solution of methylene blue. The release of the dye in 100 ml water was studied at 37° C. by monitoring the increasing absorbance at 664 nm. The resulting release curve is shown in FIG. 2, which gives the amount of dye released versus square root of time. As seen in the figure the curve is linear between about 20 min to 24 h, which is to be expected for a release preparation of the matrix type ("Sustained and Controlled Release Drug Delivery Systems", Marcel Dekker Inc. (1978)). As an alternative to the monoolein mentioned above, an industrially distilled product was used.

EXAMPLE 2

Figure 3:
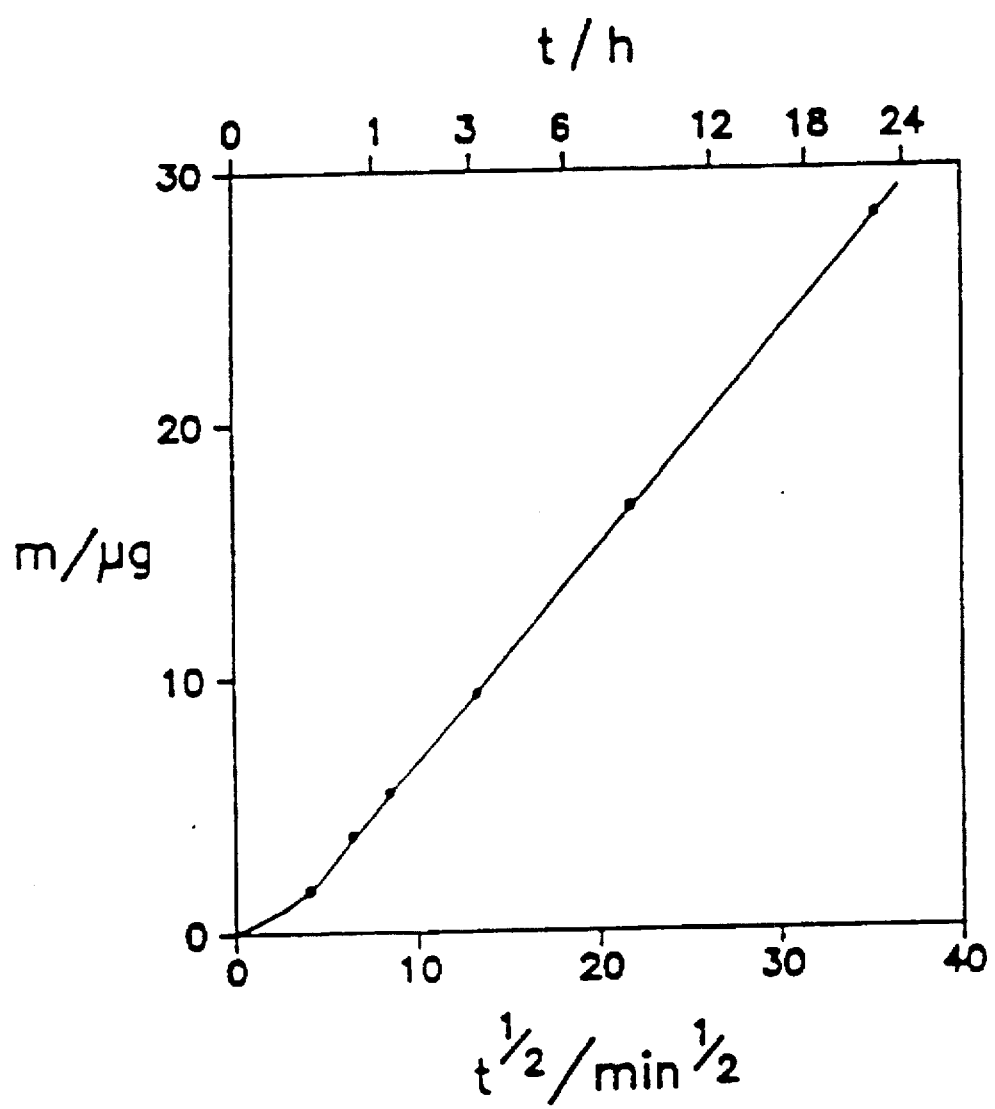
FIG. 3 shows the amount of dye released versus square root of time for the system monoolein-egg yolk lecithin-water (including dye) at 37° C.

FIG. 3 shows the release profile for one cubic phase where egg yolk lecithin was incorporated. The composition of the cubic phase was (monoolein/egg yolk lecithin/dye-solution) (48.0/12.0/40.0) (w/w). The figure clearly reveals that the release profile may be altered by the addition of egg yolk lecithin.

EXAMPLE 3

Figure 4:
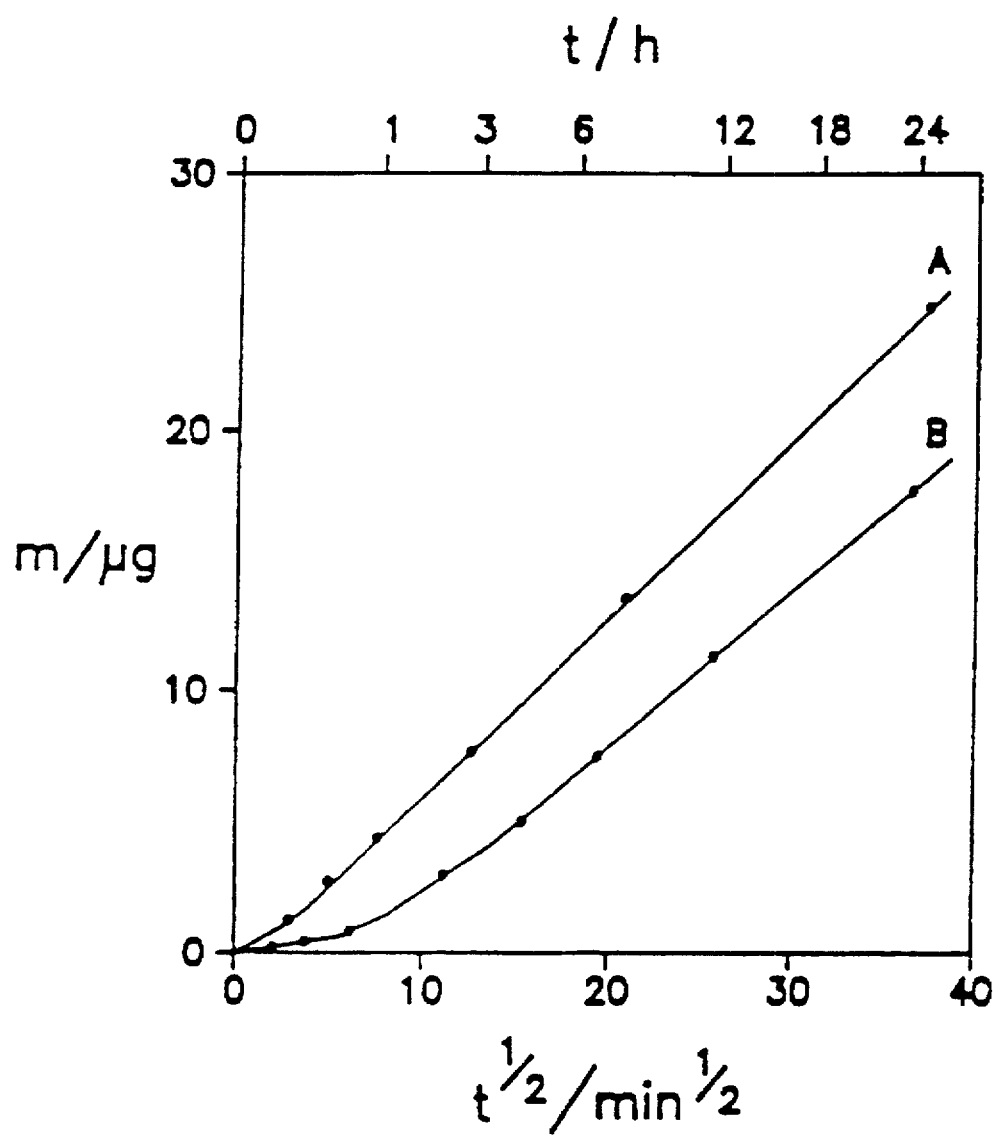
FIG. 4 shows the amount of dye released versus square root of time for the system monoolein-glycerol-water (including dye) at 37° C.

FIG. 4 shows corresponding release curves for cubic phase where some water were replaced by glycerol. The compositions of the two cubic phases are (monoolein/glycerol/dye-solution) (w/w):

A=(60.0/4.0/36.0)

B=(60.0/10.0/30.0)

It is evident from FIG. 4 that even a small amount of glycerol has a large effect one release rate of methylene blue.

The following three examples describe how to make cubic liquid crystalline phases with pharmaceutical compounds, either dissolved or dispersed:

EXAMPLE 4

0.6 g of monoolein was mixed with 0.4 g of a 7.5% (w/w) aqueous solution of terbutaline sulphate (other names are Bricanyl® and Filair®; used for the treatment of asthma) in an ampoule, which was sealed. After 24 h at 40° C. a glass-clear cubic liquid crystalline phase was obtained. It is also possible to replace up to 15% (w/w) of the water by glycerol, and still obtain the cubic phase.

EXAMPLE 5

0.6 g of monoolein was mixed with 0.4 g water and 0.5 mg of oestriol (other names are Ovesterin®, Triodurin® and Triovex®; used for the treatment of vaginal disease). The ampoule was sealed and after about 24 h at 40° C. a glass-clear cubic liquid crystalline phase was obtained.

EXAMPLE 6

0.6 g of monoolein was mixed with 0.4 g of water and 0.2 g of 2-amino-1-phenylpropanol hydrochloride (other names Lunerin® and Rinomar®; used for treatment of disease in the nose). The mixture was placed at 40° C. for about 24 h, and the saturated cubic phase obtained (with respect to 2-amino-1-phenylpropanol hydrochloride) was heated to 100° C. for about ten minutes, and then shaked extensively during cooling, in order to disperse the rest of the drug in the cubic phase.

Transdermal application of cubic phases

The following example describes a method to make a mixture of monoolein and egg yolk lecithin on a molecular level, and how to use this mixture together with nitroglycerin and water to make a cubic phase suitable for transdermal controlled-release.

EXAMPLE 7

A mixture of 90 g monoolein and 30 g egg yolk lecithin is dissolved in 800 g of ethanol, 95% (v/v). The solvent is evaporated in order to get a molecular mixture of the lipids. 6% (w/w) nitroglycerin is solved in a glycerol-water 1:1 (w/w) mixture and 80 g of this solution is added to the 120 g lipid mixture obtained above. Equilibrium has been reached when a glass-clear gel-like phase has been obtained. This phase is suitable for transdermal controlled-release of nitroglycerin from a depot-plaster in the range of 0.1–5 mg nitroglycerin absorbed per hour.
Coating with cubic phases for protection The example below describes how the cubic liquid crystalline phase precursor may be used to protect a patient against bad taste and to protect the drug against degradation in the stomach. The drug is benzylpenicillin.

EXAMPLE 8

Benzylpenicillin is pressed into tablets of 0.3 g according to conventional techniques. The tablets are coated with monoolein in an ethanol solution using a fluidized bed, and then covered with a thin film of sugar. Such a coating will also give a total protection against taste disturbance due to the penicillin in the mouth, and a controlled-release function so that the benzylpenicillin is protected against acidic degradation in the stomach, whereas it is exposed for absorption in the small intestine due to the solubilization of the coat by bile acids from the bile.
Reversed hexagonal liquid crystalline phase preparation Galactoyl-diglycerides can be isolated from plants or prepared synthetically, and monogalactoyl-diglycerides form reversed hexagonal phases with any amount of water above 5% (w/w). The example below describes a method to prepare reversed hexagonal liquid crystalline phase from galactoyl-diglycerides.

EXAMPLE 9

Saturate water with acetylsalicylic acid and add 20 g of this solution to 80 g of monogalactoyl-diglyceride isolated from wheat lipids by column chromatography. The wheat lipids are easily obtained by ethanol extraction of wheat flour or wheat gluten. After a few days equilibrium has been reached as seen by the homogeneous appearance in the polarizing microscope.
Spray inhalator in the form of a precursor of a cubic phase The final example describes a method to make a precursor of the cubic phase in liquid form, which is suitable for spray inhalation of insulin.

EXAMPLE 10

A saturated solution of insulin in water is prepared. 10% (w/w) of this solution is added to 90% (w/w) of liquid monolinolein. The resulting liquid is atomized to an aerosol by conventional spray technique for inhalation.

The above described system provides a possibility for absorption of native insulin for diabetes. Insulin keeps its native conformation both in the liquid phase used to give the aerosol as well as in the cubic phase-formed at contact between droplets and water in the mucous layer where absorption takes place.

We claim:

1. A composition for controlled release of selected bioactive material, said composition comprising:

(a) a cubic liquid crystalline phase comprising a lipid bilayer and a hydrophilic domain, said lipid bilayer comprising one or more lipids selected from the group consisting of monoglycerides, phospholipids, galactolipids, and mixtures thereof, and (b) an effective amount of bioactive material preferentially partitioned in one of said hydrophilic domain and said lipid bilayer.

2. A composition according to claim 1 wherein said hydrophilic domain includes water therein.

3. A composition according to claim 2 wherein said hydrophilic domain further includes glycerol therein.

4. A composition according to claim 1 wherein said cubic liquid crystalline phase includes monoglyceride therein.

5. A composition according to claim 1 wherein said bioactive material is a pharmaceutical compound selected from the group consisting of antibiotics, proteins, steroids, vitamins and nucleic acids.

6. A composition for controlled release of selected bioactive material, said composition comprising:

(a) a reversed hexagonal liquid crystalline phase having a lipid bilayer and a hydrophilic domain, said lipid bilayer comprising one or more lipids selected from the group consisting of monoglycerides, phospholipids, galactolipids, and mixtures thereof; and (b) an effective amount of selected bioactive material preferentially partitioned in one of said hydrophilic domain and said lipid bilayer.

7. A composition according to claim 6 wherein said hydrophilic domain includes water therein.

8. A composition according to claim 7 wherein said hydrophilic domain further includes glycerol therein.

9. A composition according to claim 6 wherein said bioactive material is a pharmaceutical compound selected from the group consisting of antibiotics, proteins, steroids, vitamins and nucleic acids.

10. A method of delivering a bioactive material to a patient, said method including the steps of:

(a) administering, in vivo, a composition comprising:

(i) a cubic liquid crystalline phase including a lipid bilayer and a hydrophilic domain, said lipid bilayer comprising one or more lipids selected from the group consisting of monoglycerides, phospholipids, galactolipids, and mixtures thereof; and (ii) an effective amount of bioactive material selectively partitioned in one of said lipid bilayer and said hydrophilic domain; and (b) allowing an effective amount of bioactive material to dissociate from said cubic liquid crystalline phase.

11. A method according to claim 10 wherein said cubic liquid crystalline phase is formed prior to said composition being administered in vivo.

12. A method according to claim 10 wherein said bioactive material is a pharmaceutical compound selected from the group consisting of antibiotics, proteins, steroids, vitamins and nucleic acids.

13. A method according to claim 10 wherein said composition is positioned in a body cavity of a patient to be treated.

14. A method for delivering a bioactive material to a patient, said method including the steps of:

(a) administering, in vivo, a composition comprising:
  (i) a reversed hexagonal liquid crystalline phase including a lipid bilayer and a hydrophilic domain, said lipid bilayer comprising one or more lipids selected from the group consisting of monoglycerides, phospholipids, galactolipids, and mixtures thereof; and
  (ii) an effective amount of bioactive material selectively partitioned in one of said lipid bilayer and said hydrophilic domain; and
(b) allowing an effective amount of bioactive material to dissociate from said reversed hexagonal liquid crystalline phase.

15. A method according to claim 14 wherein said reversed hexagonal liquid crystalline phase is formed prior to said composition being administered in vivo.

16. A method according to claim 14 wherein said bioactive material is a pharmaceutical compound selected from the group consisting of antibiotics, proteins, steroids, vitamins and nucleic acids.

17. A method according to claim 14 wherein said composition is positioned in a body cavity of a patient to be treated.

18. A lipid composition for controlled release of a biologically active material which comprises:

(a) monoolein and at least one oil in amounts necessary to form a reversed hexagonal liquid crystalline phase having a lipid bilayer and a hydrophilic domain upon contact with water; and (b) an effective amount of a bioactive material selected from the group consisting of antibiotics, proteins, steroids, vitamins and nucleic acids.

19. A lipid composition for controlled-release of biologically active material which comprises:

(a) monoolein and glycerol in amounts necessary to form a reversed hexagonal liquid crystalline phase having a lipid bilayer and a hydrophilic domain upon contact with water; and (b) an effective amount of a bioactive material selected from the group consisting of antibiotics, proteins, steroids, vitamins, and nucleic acids.

* * * * *